(12) United States Patent
Powlan

(10) Patent No.: US 8,535,322 B1
(45) Date of Patent: Sep. 17, 2013

(54) HIP NAIL AND INERTIAL INSERTION TOOLING

(71) Applicant: Roy Y. Powlan, Lafayette, CA (US)

(72) Inventor: Roy Y. Powlan, Lafayette, CA (US)

( * ) Notice: Subject to any disclaimer, the term of this patent is extended or adjusted under 35 U.S.C. 154(b) by 0 days.

(21) Appl. No.: 13/694,203

(22) Filed: Nov. 7, 2012

(51) Int. Cl.
*A61F 2/46* (2006.01)
(52) U.S. Cl.
USPC .......................................... 606/89; 606/86 R
(58) Field of Classification Search
USPC ...... 606/53, 60, 246–279, 300–320, 325–328; 623/23.26–23.27
See application file for complete search history.

(56) References Cited

U.S. PATENT DOCUMENTS

| | | | | |
|---|---|---|---|---|
| 1,091,674 A * | 3/1914 | Lee | ................. | 411/176 |
| 2,077,804 A * | 4/1937 | Morrison | ......................... | 606/68 |
| 2,631,584 A * | 3/1953 | Purificato | ......................... | 606/68 |
| 2,685,877 A * | 8/1954 | Dobelle | ..................... | 623/23.11 |
| 3,024,785 A * | 3/1962 | Dobelle | ..................... | 623/23.26 |
| 3,103,926 A * | 9/1963 | Cochran et al. | ............... | 606/319 |
| 3,497,953 A * | 3/1970 | Weissman | ..................... | 433/173 |
| 3,791,380 A * | 2/1974 | Dawidowski | .................. | 606/68 |
| 3,892,232 A * | 7/1975 | Neufeld | ............. | 606/80 |
| 4,236,512 A * | 12/1980 | Aginsky | ........................ | 606/68 |
| 4,275,717 A * | 6/1981 | Bolesky | ......................... | 606/63 |
| 4,498,468 A * | 2/1985 | Hansson | ......................... | 606/68 |
| 4,519,100 A * | 5/1985 | Wills et al. | ...................... | 606/63 |
| 4,530,355 A * | 7/1985 | Griggs | .......................... | 606/105 |
| 4,759,352 A * | 7/1988 | Lozier | ............................ | 606/66 |
| 4,790,304 A * | 12/1988 | Rosenberg | ................... | 606/916 |
| 5,217,462 A * | 6/1993 | Asnis et al. | ................... | 606/916 |
| 5,217,486 A * | 6/1993 | Rice et al. | ...................... | 606/232 |
| 5,429,641 A * | 7/1995 | Gotfried | ......................... | 606/67 |
| 5,514,138 A * | 5/1996 | McCarthy | ....................... | 606/65 |
| 5,534,004 A * | 7/1996 | Santangelo | ..................... | 606/68 |
| 5,643,321 A * | 7/1997 | McDevitt | ...................... | 606/232 |
| 5,810,820 A * | 9/1998 | Santori et al. | ................... | 606/63 |
| 5,836,950 A * | 11/1998 | Hansson | ......................... | 606/65 |
| 5,843,127 A * | 12/1998 | Li | ............................... | 606/232 |
| 5,971,986 A * | 10/1999 | Santori et al. | ................... | 606/62 |
| 5,976,139 A | 11/1999 | Bramlet | | |
| 6,077,264 A * | 6/2000 | Chemello | ....................... | 606/67 |
| 6,183,474 B1 * | 2/2001 | Bramlet et al. | ................. | 606/66 |
| 6,443,954 B1 | 9/2002 | Bramlet | | |
| 6,447,546 B1 * | 9/2002 | Bramlet et al. | ............ | 623/17.16 |
| 6,558,388 B1 * | 5/2003 | Bartsch et al. | .................. | 606/62 |
| 6,575,974 B2 * | 6/2003 | Gotfried | ......................... | 606/67 |
| 6,648,889 B2 | 11/2003 | Bramlet | | |
| 6,695,844 B2 * | 2/2004 | Bramlet et al. | ................. | 606/66 |

(Continued)

OTHER PUBLICATIONS

Ola Olsson; Lunds University, "Alternative techniques in hip fracture surgery," University Dissertation, Helsingborg Hosp., Helsingborg, Sweden.

(Continued)

*Primary Examiner* — Eduardo C Robert
*Assistant Examiner* — Lynnsy Schneider

(57) ABSTRACT

A hip nail is inserted across a fracture of the proximal femur and locked in place by a plurality of tangs that are forcibly deployed from within the leading end of the nail into the head of the femur by means of blows on a central driving shaft, while a recoil transferring tube and tool shaft, and the inertia of a mass releasably attached to the base of the nail absorbs the recoil, enabling the nail to remain stationary relative to the bone, thereby enabling the tangs to deploy in a generally curvilinear perpendicular direction without twisting or unwanted distortion.

1 Claim, 3 Drawing Sheets

(56) References Cited

U.S. PATENT DOCUMENTS

| | | | |
|---|---|---|---|
| 7,029,476 B2* | 4/2006 | Hansson | 606/304 |
| 7,118,572 B2* | 10/2006 | Bramlet et al. | 606/66 |
| 7,211,086 B2* | 5/2007 | Biedermann | 606/308 |
| 7,780,710 B2* | 8/2010 | Orbay et al. | 606/286 |
| 7,850,699 B2* | 12/2010 | Hansson | 606/104 |
| 7,931,653 B2* | 4/2011 | Hansson | 606/63 |
| 8,083,776 B2* | 12/2011 | Alvarez | 606/265 |
| 8,157,801 B2* | 4/2012 | Doubler et al. | 606/64 |
| 8,197,519 B2* | 6/2012 | Schlaepfer et al. | 606/278 |
| 8,262,709 B1* | 9/2012 | Powlan | 606/281 |
| 8,308,782 B2* | 11/2012 | Jackson | 606/308 |
| 8,337,495 B1* | 12/2012 | Powlan | 606/63 |
| 2004/0002735 A1* | 1/2004 | Lizardi et al. | 606/232 |
| 2004/0049192 A1* | 3/2004 | Shimizu | 606/62 |
| 2009/0112208 A1* | 4/2009 | Borgia et al. | 606/59 |
| 2010/0057141 A1* | 3/2010 | Abdelgany et al. | 606/310 |
| 2010/0280556 A1* | 11/2010 | Hansson | 606/286 |
| 2011/0066190 A1* | 3/2011 | Schaller et al. | 606/301 |
| 2012/0197315 A1* | 8/2012 | Kim | 606/305 |
| 2012/0310291 A1* | 12/2012 | Jackson | 606/305 |

OTHER PUBLICATIONS

Olsson et al., Extracapsular hip fractures: Twinhook or lag screw? Helsingborg Hosp., Helsingborg, Sweden.

Hagino, T. rt al., Twin hook fixation for femoral fractures. Journal of Orthopedic Surgery, Aug. 2008, 16(2), p. 162-64.

* cited by examiner

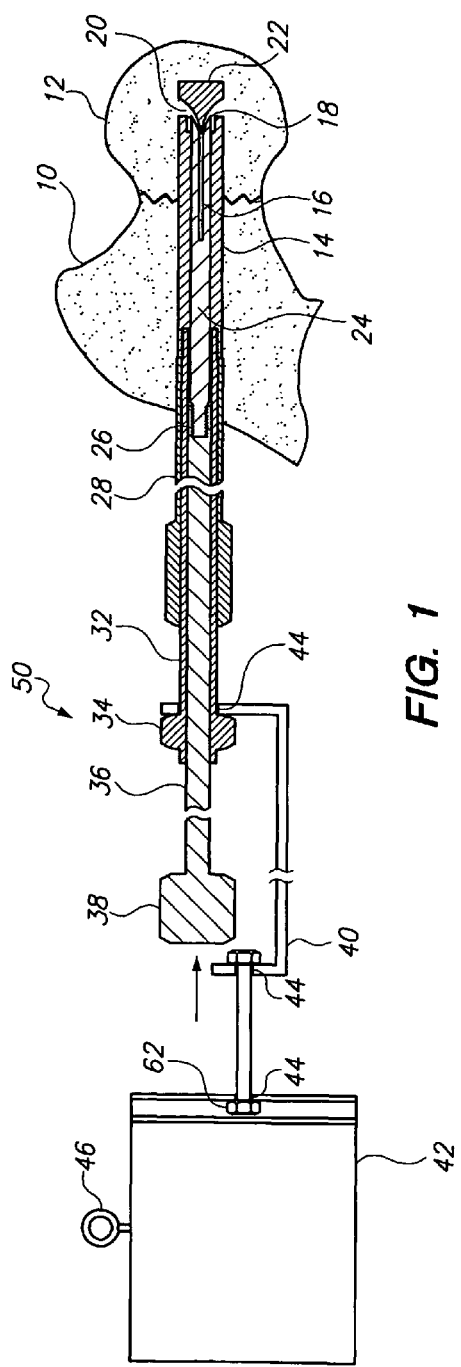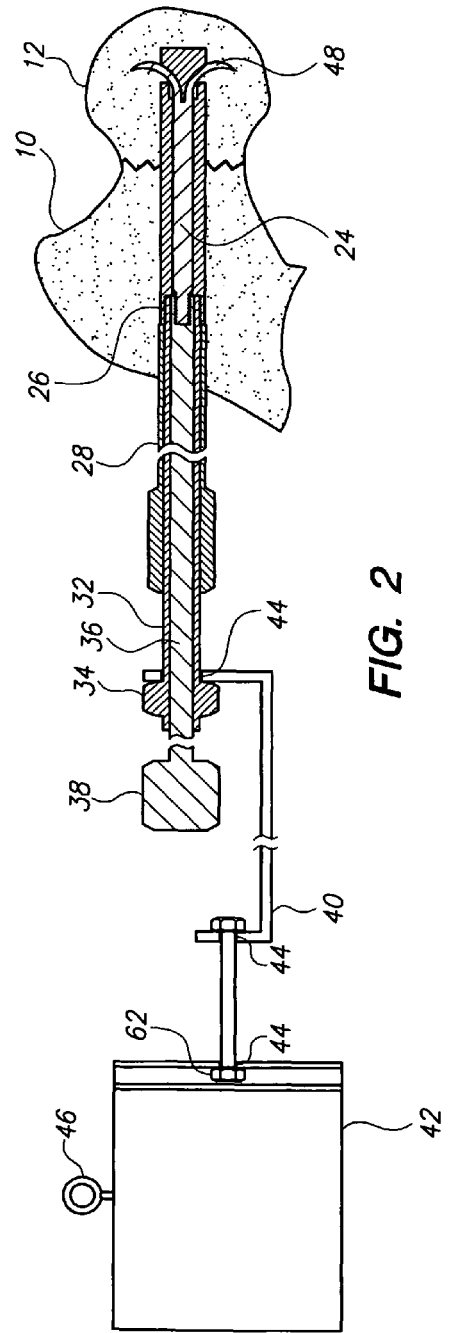

HIP NAIL AND INERTIAL INSERTION TOOLING

FIELD OF THE INVENTION

This invention generally relates to the combination of a surgical apparatus for rigidly inter-connecting fractured bones of the extremities, in particular, the proximal femur, together with a method and tooling for its insertion

BACKGROUND OF THE INVENTION

Compression screw systems are widely used to treat fractures of the proximal femur, including those of the femoral neck and the peri-trochanteric areas of the bone.

The systems generally consist of a lag screw inserted from the lateral side of the femur, across the fracture and into the head of the femur, holding the bone fragments together. The trailing end of the screw may be supported either by a cortical side plate with a tubular barrel through which the nail can slide, or by an intramedullary nail with a transverse opening, that has been inserted longitudinally into the medullary canal of the femur.

Their wide usage is based on their ability to compress the bone ends together to promote healing, and to permit lateral sliding as some absorption with shortening of the healing bone takes place.

Effective as lag screws are, however they have some disadvantages. The bulk of the threaded end displaces valuable viable bone and can lead to death of the head of the femur. The threads can pull out of osteoporotic bone, defeating their purpose. Rotation of the head of the femur around the nail at the fracture site with certain patient activities can also interfere with fracture healing, especially with high neck fractures.

Over the past several decades, numerous inventions have been devised in an attempt to circumvent the problems associated with the use of lag screws, chiefly among them being the use of prongs, tangs or hooks that that are extruded from or near the tip of the nail to lock into the surrounding bone, yet are not widely used, possibly because of problems relating to their deployment in the femur, and to their removal.

The present invention overcomes problems of deployment by using a nail with locking tangs, wherein the tangs are deployed by an impulse force applied to a central drive-shaft which drives and progressively forces the tangs through die-like openings into the dense bone of the femoral head. The resulting recoil which would normally cause the entire nail with its tangs to be driven further into the bone, or which could cause distraction of the fracture, is directed by specialized tooling to a location outside of the immediate operative site, thereby enabling deployment of the tangs while the nail itself remains stationary relative to the surrounding bone.

SUMMARY OF THE INVENTION

It comprises a combination of a nail employing a plurality of tangs for the fixation of fractures of a bone, in particular the hip region of the femur, together with tooling and method for deploying and retracting the tangs.

Whereas the prior art deployed the tangs gradually from within a hip nail by means of worm gears, traction on a drawbar, pressure on a drawbar by means of a screw mechanism, or by a molly-like central screw assembly, this invention avoids the use of small, complex functioning parts, which can bend or break during deployment into dense bone, and which can twist or deform the tangs from their normal configuration, making removal of the nail difficult.

Instead, this apparatus deploys the locking tangs by means of forcible blows on a centrally located drive shaft which is releasably attached to the base of the tang body, causing the tangs to deploy into the surrounding bone. As with any directed force, there exists an equal and opposite counterforce, a "recoil", which if not controlled, would cause the entire nail together with the tangs to translate further into the bone, rather than having the tangs alone translate into the bone, while the nail sheath itself remains unmoved.

This apparatus neutralizes the recoil by means of tooling that redirects the counterforce away from the nail to a heavy mass outside of the patient's body, using the inertia of the mass to absorb the recoil energy of the blow.

The first end of the recoil transferring tube is releasably fastened to the trailing end of the nail sheath, and the second end to the recoil transferring tool shaft, which in turn is releasably fastened to an arbitrarily configured inertial mass, for example, a mass composed of a heavy material such as lead, to make it more compact, measuring seven inches square and an inch thick, weighing approximately twenty pounds, mounted on a stand an appropriate short distance from the operative site, and covered with sterile drapes. The weight of the inertial mass could be more or less than the example of twenty pounds, depending on the desired amount of relative motion of the assembly's components during deployment, and could be of any suitable configuration consistent with its function in the operating room.

Furthermore, since the acceleration of the nail and the attached large inertial mass resulting from the force impressed upon them during the tang deployment is proportional to the total mass of the tang body and the tangs which would be minimal, the resulting acceleration of the nail and inertial mass would be miniscule in comparison.

Alternatively, the second end of the intermediate tool rod could be releasably fastened to a rigid stanchion or bracket fastened to the operating table, but this would not be as practical as using the inertia of a moveable mass which can be quickly and easily moved into alignment with the longitudinal axis of the embedded hip nail and its recoil transferring tube.

As a result of using a tool which incorporates an inertial mass outside of the patient's body to absorb and counteract the longitudinal driving force needed to deploy the locking tangs, the tangs are able to be properly deployed without significant longitudinal translation of the nail itself. This avoids the tangs being twisted, bent or distorted and possibly being extruded into a longitudinal position rather than becoming essentially perpendicular to the long axis of the nail. In addition, there is less of a tendency for the fracture to become dis-impacted.

Further advantages of this method of using an external inertial mass to absorb the recoil is that it is simple and easy to use, and it avoids using complex insertion hardware. The use of tangs in the head of the femur instead of lag screw threads, tends to better resist pull-out, especially in osteoporotic bone, and better controls rotation of the head of the femur during healing. Because of their smaller bulk, they also interfere less with the circulation of blood in the head of the femur, thereby promoting healing. A further advantage of this nail is that it is easily adaptable for use with either a known cortical side plate or the known transverse opening of a centrally placed intramedullary rod, each configured to prevent rotation of the nail, yet permitting controlled sliding.

Another significant advantage of using impulse force such as with a mallet to drive the tangs into a proper position within the dense bone of the femoral head is that considerable force is needed to progressively transform the tangs from a linear state to a curvilinear state, especially if the deployed tangs have been made wide enough and thick enough to withstand a strong traction force placed on them without flexing or deforming, which would be difficult to achieve by other means.

The locking tangs can be easily and quickly withdrawn back into the body of the nail for its removal by re-attaching the deployment assembly and reversing the direction of the forces.

BRIEF DESCRIPTION OF THE DRAWINGS

FIG. 1 is a sectional view showing the entire assembly with the nail embedded in a bone, the attached tool rods, the attached intermediate tool rod, and the attached inertial mass. The tangs have not been deployed.

FIG. 2 is a sectional view similar to FIG. 4, but showing the tangs having been deployed.

DETAILED DESCRIPTION OF THE DRAWINGS

Figure 3:
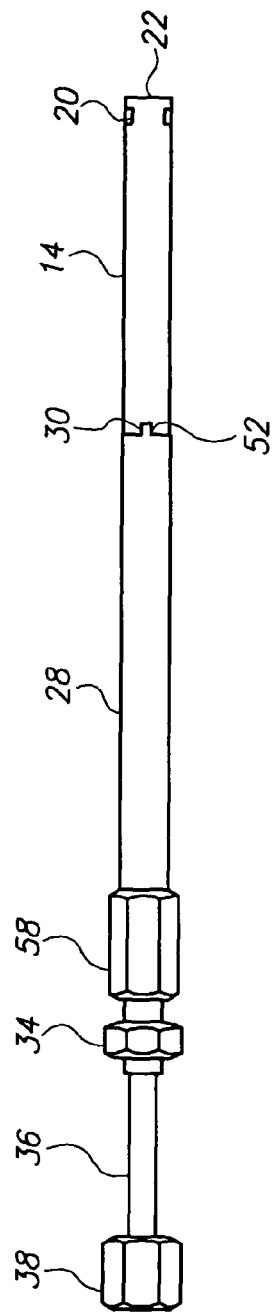
FIG. 3 and FIG. 4 are orthogonal views showing the assembled nail and tool rods, with FIG. 3 showing the assembly before deployment of the tangs, and FIG. 4 the assembly after deployment.

FIG. 1 is a sectional view showing the complete hip nail and insertion tooling assembly. The tubular nail sheath 14 with the tip of the nail 22 is embedded in the femoral head 12 across the fracture 10.

The tang bearing rod 24, is shown within the nail sheath 14, with the un-deployed locking tangs 16 with their tips 22 positioned in the openings with sloping floors 20. The locking tangs in one embodiment, are formed from the leading end of the tang bearing rod, and in another embodiment are formed separately and welded to the end of the rod, depending on the requirements of the tangs, such as their malleability and stiffness.

The angle of the slope of the floors of the openings 20 determines the angle of the segments, relative to the longitudinal axis of the nail after they have been extruded, which in one embodiment is approximately ninety degrees.

The trailing end of the tang bearing rod 24 is threaded for a coupling 26 with the leading end of the central driving shaft 36. The trailing end of the driving shaft is enlarged to form a striking pad 38. Mallet blows to the striking pad cause the driving shaft to drive the tang bearing rod 24 with the attached locking tangs 16 further into the tubular nail sheath 16, which causes the bone penetrating tips 18 of the locking tangs to engage with the openings with sloping floors 20 and to become deployed 48 into the femoral head 12.

The recoil of the force driving the locking tangs through the orifices, if not controlled, would also cause the nail sheath 14 to translate further into the head of the femur 12. In order to prevent this from happening, the leading end of a recoil transferring tube 32 is releasably attached to the base of the nail sheath 24 with the threaded coupling 26. A recoil transferring tool shaft 40 is releasably attached to the trailing end of the tube 32 by means of a slot 44 which is braced against the collar 34. The trailing end of the shaft 40 is the releasably attached to an arbitrarily configured mass 42 by means of the connecting rod 62 and slot 44

The length of the shaft 40 is predetermined to extend from the immediate operative site, to the mass 42, which is positioned a short distance away from the operative site, for example, but not limited to, a distance of approximately twenty-four inches, a distance consistent with practical considerations such as sterile requirements and access to the striking pad 38.

The mass 42 could be of any practical configuration, but in one embodiment is a seven inch square, one inch thick mass of lead, weighing approximately twenty pounds with an attaching slot 44 for the releasable attachment of the shaft 40 and connecting rod 62. A supporting loop 46 enables the mass to be supported from a stand (not shown) that enables it to be quickly moved into alignment with the central driving shaft 36.

As the central driving shaft 36 and the attached locking tangs are being driven forward through the nail sheath 14, the recoil is transferred back through the recoil transferring tube 32, and through the recoil transferring tool shaft 40, and connecting rod 62 to the inertial mass 42, which because of its very large inertia, absorbs the force of the recoil. As a result, the locking tangs 16 are driven cleanly through the openings 20, into the femoral head, while the nail sheath 14 remains stationary relative to the surrounding bone.

FIG. 1 also shows the tubular rotatable socket tool 28 which is positioned slidingly rotatable on the recoil transferring tube 32. Its leading end has tabs 30 (FIGS. 3 and 4) that interdigitate with notches 52 in the nail sheath 14 and which enable rotation of the nail sheath. Its trailing end is enlarged and hexagon shaped 58 to enable its manual rotation. Its shape could be that of a handle, for example, or any configuration enabling manual manipulation of the socket tool.

FIG. 2 is a sectional view similar to FIG. 1 but showing the central drive shaft 36 and the attached locking tangs 16 having been driven through the nail sheath 14, and the openings 20 to become deployed 48 in the femoral head 12.

FIG. 3 is an orthogonal view showing the assembled nail sheath 14 with the insertion tooling prior to the deployment of the locking tangs 16.

Figure 4:
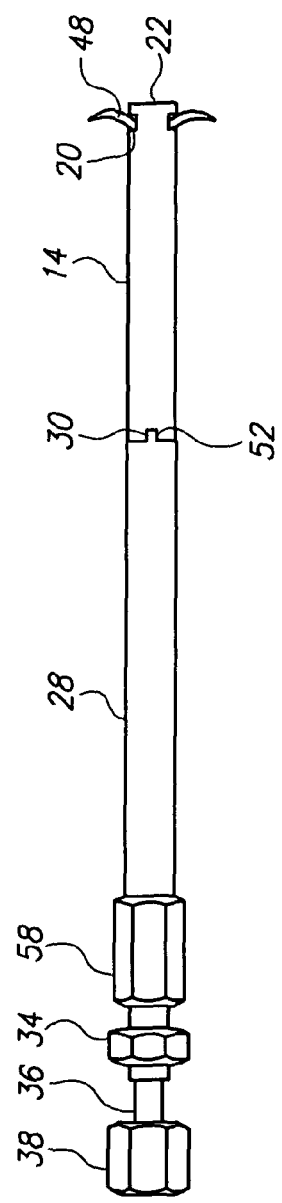

FIG. 4 is an orthogonal view similar to FIG. 3 but showing the deployed locking tangs 48 having been driven out by the central driving shaft 36, through the openings 20 at the tip of the nail 22. Not shown is the recoil transferring tool shaft or the inertial mass 42.

Figure 5:
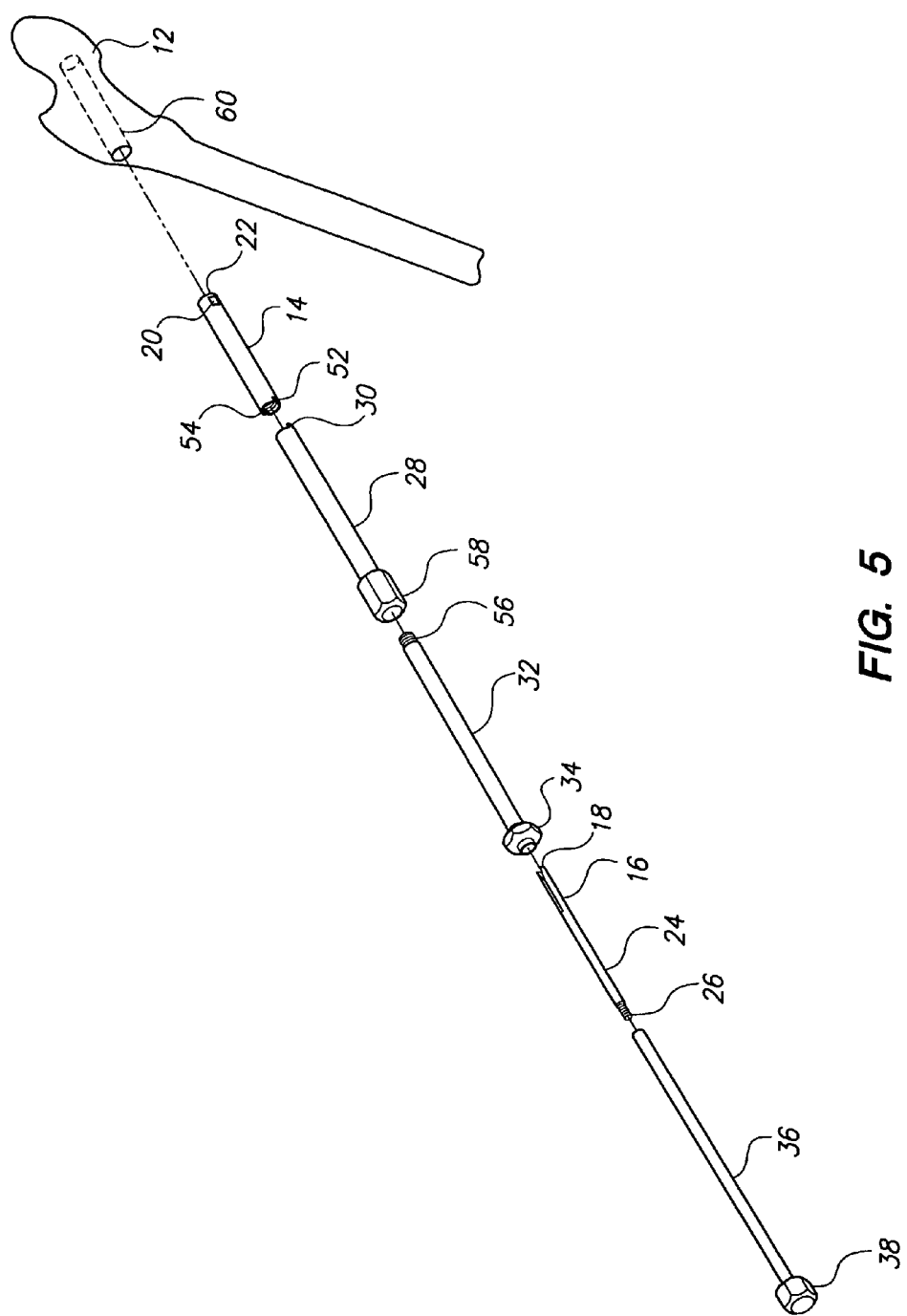
FIG. 5 is an exploded perspective view of a nail, tang body with tangs, and tool rods, together with an opening in a bone.

FIG. 5 is an exploded view of the hip nail and insertion tooling assembly 50, together with a section of femur and femoral head 12 with an opening 60 for the insertion of the nail 14. It shows how the central driving shaft 36, the tang bearing rod 24 with locking tangs 16, and the recoil transferring tube 32 telescope into the rotatable socket tool 28 which in turn engages with the base of the nail sheath 14 in a non-rotatable coupling with tabs 30 and notches 52. Not shown is the recoil transferring tool shaft 40 or the inertial mass 42. Also shown is the striking pad 38, the collar 34 that enables coupling with the recoil transferring tool shaft and the inertial mass (both not shown), and the internal threads 54 that enable coupling with the threads 56 on the leading end of the recoil transferring tube 32.

DRAWINGS REFERENCE NUMERALS WORKSHEET

Part Name

| | |
|---|---|
| 10 | Fractured Femur |
| 12 | Femoral Head |
| 14 | Tubular Nail Sheath |
| 16 | Locking Tangs |
| 18 | Bone penetrating tips |
| 20 | Openings with sloping floors |
| 22 | Tip of Nail |

| | |
|---|---|
| 24 | Tang bearing rod |
| 26 | Threaded coupling |
| 28 | Rotatable socket tool |
| 30 | Socket tool tabs |
| 32 | Recoil transferring tube |
| 34 | Collar |
| 36 | Central driving shaft |
| 38 | Striking pad |
| 40 | Recoil transferring tool shaft |
| 42 | Inertial mass |
| 44 | Attaching slots |
| 46 | Support loop |
| 48 | Deployed locking tangs |
| 50 | Hip nail and inertial insertion tooling |
| 52 | Notch for socket tool |
| 54 | Internal threads |
| 56 | Threads for coupling base of nail |
| 58 | Handle of socket tool |
| 60 | Opening in bone for nail |
| 62 | Connecting rod |

I claim:

1. A combination of an intramedullary device for mending a fractured bone and tooling for its insertion into the bone comprising:

a known hip fracture nail assembly, said hip fracture nail assembly comprising:

an elongate tubular nail sheath, said elongate tubular nail sheath comprising:

a leading end and a trailing end, and with said leading end of said tubular nail sheath comprising a plurality of locking tang redirecting channels and orifices, said locking tang redirecting channels and orifices configured to redirect a plurality of elongate locking tangs from within said tubular nail sheath into surrounding bone, and with said trailing end of said tubular nail sheath comprising a plurality of notches, said plurality of notches enabling rotation of said tubular nail sheath;

an elongate central tang bearing rod, with a first end and a second end, and with said first end of said central tang bearing rod comprising said plurality of elongate locking tangs, and with said elongate locking tangs configured to enable their extrusion through said plurality of said locking tang redirecting channels, and with said locking tang redirecting channels comprising a plurality of circumferential radially disposed openings with sloping floors through which said elongate locking tangs are able to be urged from a longitudinal alignment within said elongate tubular nail sheath to a generally curvilinear perpendicular alignment external to said elongate tubular nail sheath, and with the leading end of each locking tang comprising a sharpened bone penetrating means, and with said trailing end of said central tang bearing rod comprising an externally threaded means for the releasable attachment of an elongate central driving shaft, said driving shaft comprising a first end and a second end, and with said first end of said elongate central driving shaft comprising a threaded means for releasable coupling with said tang bearing rod, and with said second end comprising a striking pad, said striking pad configured to accept mallet blows, and to enable said central driving shaft to forcibly drive said locking tangs through said locking tang redirecting channels and orifices and to emerge curvilinear and generally perpendicular to the sheath and enable said tangs to penetrate into surrounding bone; and said trailing end of said elongate nail sheath comprising an internally threaded means with a releasably attached elongate tubular recoil transferring tube, said recoil transferring tube comprising a leading end and a trailing end, said leading end of said recoil transferring tube comprising an externally threaded means for its releasable attachment to said trailing end of said elongate tubular nail sheath, said trailing end of said recoil transferring tube comprising a circumferential collar, said collar releasably attached to a leading end of a recoil transferring tool shaft, said recoil transferring tool shaft comprising the leading end and a trailing end, said leading end of said recoil transferring tool shaft comprising a means for the releasable attachment of said trailing end of said recoil transferring tube, said means comprising a slotted opening, and with said trailing end of said recoil transferring tool shaft comprising a connecting rod releasably attached to an inertial mass, and with said recoil transferring tool shaft configured with sufficient length to enable its releasable attachment to the inertial mass positioned externally to the operative site consistent with sterility requirements, said inertial mass comprising an arbitrarily configured mass of weight and size sufficiently large to absorb the recoil resulting from the forcible urging of said plurality of elongate locking tangs through the plurality of locking tang redirecting channels and orifices; and with a rotatable socket tool, said tool comprising an elongate tubular sheath with a diameter similar to that of said tubular nail sheath, and with its inside diameter enabling the positioning of said recoil transferring tube through it, and with said rotatable socket tool comprising a leading end and a trailing end, and with said leading end comprising a plurality of tabs, said tabs configured to interdigitate with said plurality of notches at said trailing end of said tubular nail sheath, and with said trailing end of said rotatable socket tool comprising means for its manual rotation, said means enabling the selectable axial rotation of the nail sheath;

whereby said inertial mass absorbs said recoil resulting from the forcible urging of said plurality of elongate locking tangs through said plurality of locking tang redirecting channels and orifices of said tubular sheath, thereby enabling the deployment of said locking tangs without distortion into surrounding bone while said tubular sheath remains stationary relative to said surrounding bone.

* * * * *